United States Patent
Steinborn et al.

(10) Patent No.: US 7,175,172 B2
(45) Date of Patent: Feb. 13, 2007

(54) METHOD AND DEVICE FOR INSERTING A PLURALITY OF INDIVIDUAL SHEETLIKE FORMS OF ADMINISTRATION IN A DISPENSER BY FORMING A MULTILAYER PILE

(75) Inventors: Peter Steinborn, Neuwied (DE); Horst Dzekan, Meinborn (DE); Klaus Schumann, Neuwied (DE); Wolfgang Laux, Diez (DE); Michael Horstmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 10/658,027

(22) Filed: Sep. 9, 2003

(65) Prior Publication Data

US 2004/0046305 A1   Mar. 11, 2004

Related U.S. Application Data

(62) Division of application No. 09/622,562, filed as application No. PCT/EP99/00584 on Jan. 29, 1999, now Pat. No. 6,659,442.

(30) Foreign Application Priority Data

Feb. 19, 1998   (DE) ................................ 198 06 966

(51) Int. Cl.
*B65H 39/16*   (2006.01)
(52) U.S. Cl. ................................ 270/52.09; 270/52.07; 53/435; 53/475; 53/520; 414/789.9; 83/88; 83/90; 83/167

(58) Field of Classification Search .............. 270/52.07, 270/52.08, 52.09, 52.1, 417, 84, 922, 85, 270/86, 87, 88, 89, 90, 167; 83/167, 417, 83/84, 922, 85, 86, 87, 88, 89, 90; 414/789.9, 414/790.4; 53/435, 475, 513, 514, 520
See application file for complete search history.

(56) References Cited

U.S. PATENT DOCUMENTS

| 2,788,208 | A | * | 4/1957 | Pearce ........................ 493/324 |
| 3,249,352 | A | * | 5/1966 | Wise ....................... 270/52.09 |
| 3,332,324 | A | * | 7/1967 | Lehmacher et al. ......... 493/197 |
| 3,444,858 | A | * | 5/1969 | Russell ........................ 604/77 |

(Continued)

FOREIGN PATENT DOCUMENTS

EP   0216762   1/1991

*Primary Examiner*—Douglas Hess
(74) *Attorney, Agent, or Firm*—Jordan and Hamburg LLP

(57) ABSTRACT

A process for introducing a plurality of segregated sheet-like administration forms into a dispenser under formation of a multilayered stack for individually dosable removal, with sheet-like tapes wound-up on rolls being present as starting material, utilizes the following steps. In a first step, a number of sheet-like layers of said tapes, which number corresponds to the stack, is simultaneously drawn from a plurality of rolls. In a further step, the individual tapes are united, using guide means, to form a multilayered strand, which in yet another step, is drawn forward to a cutting station where one length of stack is severed at a time, and wherein a length segment of the multilayered strand corresponding to the stack is substantially in the dispenser prior to being severed from a remainder of the multilayered strand by the cutting device.

9 Claims, 4 Drawing Sheets

U.S. PATENT DOCUMENTS

| | | | |
|---|---|---|---|
| 3,682,468 A | * | 8/1972 | Schriber .................... 270/52.1 |
| 3,823,934 A | * | 7/1974 | Parenti et al. ................ 270/18 |
| 3,996,720 A | * | 12/1976 | Hayduchok .................. 53/435 |
| 4,029,758 A | | 6/1977 | Mlodozeniec et al. |
| 4,070,014 A | * | 1/1978 | Takahashi ................ 270/39.09 |
| 4,180,558 A | * | 12/1979 | Goldberg et al. ........... 424/443 |
| 4,406,650 A | * | 9/1983 | Felix .......................... 493/410 |
| 5,282,350 A | * | 2/1994 | Crowley ...................... 53/435 |
| 5,348,527 A | * | 9/1994 | Beckwith .................... 493/413 |
| 5,571,361 A | | 11/1996 | Stuerzel |
| 5,588,280 A | * | 12/1996 | Kotsiopoulos ............... 53/435 |
| 5,667,617 A | | 9/1997 | Fogle |

\* cited by examiner

METHOD AND DEVICE FOR INSERTING A PLURALITY OF INDIVIDUAL SHEETLIKE FORMS OF ADMINISTRATION IN A DISPENSER BY FORMING A MULTILAYER PILE

This is a Divisional Application of application Ser. No. 09/622,562, filed Sep. 20, 2000, now U.S. Pat. No. 6,659,442.

BACKGROUND OF THE INVENTION

This invention relates to a process, as well as a device, for introducing a plurality of segregated sheet-like administration forms into a dispenser under formation of a multilayered stack for individually dosable removal, with sheet-like tapes, wound in coils, being present as starting material. The administration forms may for application thereof contain therapeutic or cosmetic or food-technological products.

Flat-shaped administration forms intended for use in the oral region and on the mucous membranes of the mouth are known. Thus, U.S. Pat. No. 3,444,858 (1969) describes medicament strips on the basis of a gelatinous material.

Furthermore, proposals to use such sheets outside the medical field are known. In EP 0 216 762 there is disclosed a water-soluble sheet of starch, gelatine, glycerine or sorbite, which is coated by means of a roll coater. It is mentioned in this document that such dosage forms can also be manufactured, for example, for chemical reagents, flavours and the like.

On the market, administration forms with single-unit dispensers made from plastics material have been available since about 1995 and have become established in the fields of application of cosmetics and sweets. In this regard, mention is made here of the product by Nisshin, Japan. The single-unit dispensers contain stacks of superimposed sheet sections which permit the individual removal of the respective upper piece of sheet after opening of an opening lip.

The technical solution to the task of producing and packaging such stacks of sheet-like starting material is, however, difficult. The literature provides no practicable instructions for their manufacture. Only U.S. Pat. No. 4,180,558 describes the stacking of edible webs, which are, however, laminated together one upon another at their edges and which therefore are unsuited for the aforementioned mode of application.

Since such sheet-like administration forms tend to become statically charged owing to their small weight per unit area, e.g. between 10 and 50 $g/m^2$, and since the surfaces must be adapted so as to be slidable for ready removal of the webs, it is only with great difficulty and great expenditure of time that one succeeds in the accurately positioned cutting and superimposing of the sheet sections.

Observing the manufacturing techniques in industrial fields such as the manufacture of paper or the packaging of plastics bags does not provide any practicable suggestions for solving the problem. Although U.S. Pat. No. 4,070,014 describes the formation of stacks from two different types of paper in partially overlapping arrangement with the aid of vacuum suction transfer rolls, this technique, like the technique for stacking paper known also from U.S. Pat. No. 5,348,527, describes a comparatively time-consuming process involving individual cuts from a roll and individual deposition on a stack.

U.S. Pat. No. 4,406,650 describes the formation of a web of paper from a roll, said web being folded in a zig-zag configuration and from which, by means of cutting, there results a stack. A disadvantage of this approach are the cuttings of the material. If the upper and bottom faces of the web have different structures, or in the case of undulation, it is not possible to stack the individual sheets with their original upper side facing upwards.

Starting from the aforementioned state of the art, it is the object of the present invention to provide a process and a device of the kind in which a plurality of administration forms are introduced into a dispenser as a stack of sheets which, while avoiding the aforementioned disadvantages and difficulties, enables the introduction into a dispenser of individually dosable sheet-like administration forms into a dispenser in a precise manner and at high process speeds and under formation of a multilayered stack, with sheet-like tapes, wound-up in coils, being present as starting material.

SUMMARY OF THE INVENTION

This object is achieved according to the invention in a process in which a multilayered strand is formed by equal-sided superimposing of the individual webs of the sheet-like intermediate product and employing guide means, jointly crosscutting the resultant strand and filling a dispenser, wherein the administration forms at the time of cross-cutting are arranged substantially within the dispenser, having been shifted to that position.

With advantage and in a surprisingly simple procedure, the stack is formed in an exact manner by simultaneous unwinding of a plurality of single rolls of the sheet-like intermediate product, superimposing of the individual webs, jointly cross-cutting the resultant multiple laminate strand and cutting the stacks into lengths, and which is conveyed into the dispenser. With great advantage, the process according to the invention is suitable for exact operation at high speed.

The intermediate product of the narrow rolls provided for this purpose consists, for example, of about 20 to 1000 m long, wound-up individual webs having the width of the product, which webs can be produced by means of roll cutting from an original broad width material. In the simplest case, a number of narrow rolls corresponding to the number of sheet pieces per dispenser is, to this end, fixed freely rollable on axles in the vicinity of a stack to be manufactured.

The rotation and unwinding directions of the rolls are preferably the same, and the material is drawn and guided jointly from all of the rolls by means of pulling devices known to those skilled in the art. The resultant multiple laminate strand is then fed to a cross-cutting device under control and leveling of the lateral edges, behind which cross-cutting device, the dispenser which is to be supplied is disposed in an open state.

The narrow rolls used may be of almost any geometry. Good results can be obtained with roll widths between 5 and 40 mm. The length of the coiled material should be at least about 20 m, preferably more than 500 m, per roll in order to avoid frequent interruption of the operation. Uniting two or more tapes in advance and simultaneous winding or unwinding is possible, but frequently leads to difficulties when many layers are being wound. Surprisingly, it has proved impossible to unwind a laminate consisting of eight or more such sheet layers in a controlled process since those laminate elements of the sheet strips which lie on the outer radius slightly longer than the inner laminate elements. When unwinding the rolls, in the case of more than four laminate layers this would lead to diverging of the webs and thus to an interruption of the process.

For this reason, winding and unwinding of rolls having few, for example, up to four laminate elements, is preferably utilized.

The type of dispenser is of no significance to the application of the present invention. Dispensers of plastics material or cardboard can be filled without problems. The opening side may, in the case of rectangular sheet sections, be at the narrow side, in which case the pre-cut narrow rolls have the width of the small side length of the rectangle.

If the narrow rolls are, however, configured in the later longitudinal dimension of the sheet sections, the opening side of the dispenser is on one of its longitudinal sides.

In the case of two-piece dispensers it would be expedient to primarily fill a bottom part, for example, configured in the shape of a drawer, and subsequently to place the top part thereon. It is also possible, however, to fill half-opened dispensers. Also, it is possible to fill sealing bags, which, especially in the case of a peelable configuration, can be used as a dispenser, for instance by placing the cut stack on the bottom web of an advancing sealable packaging material web, and subsequently, after feeding of the upper web of the packaging material, sealing the resultant bag.

Details, features and advantages of this invention will become apparent by way of example from the following explanation with reference to the accompanying drawings.

DETAILED DESCRIPTION OF THE INVENTION

Figure 1:
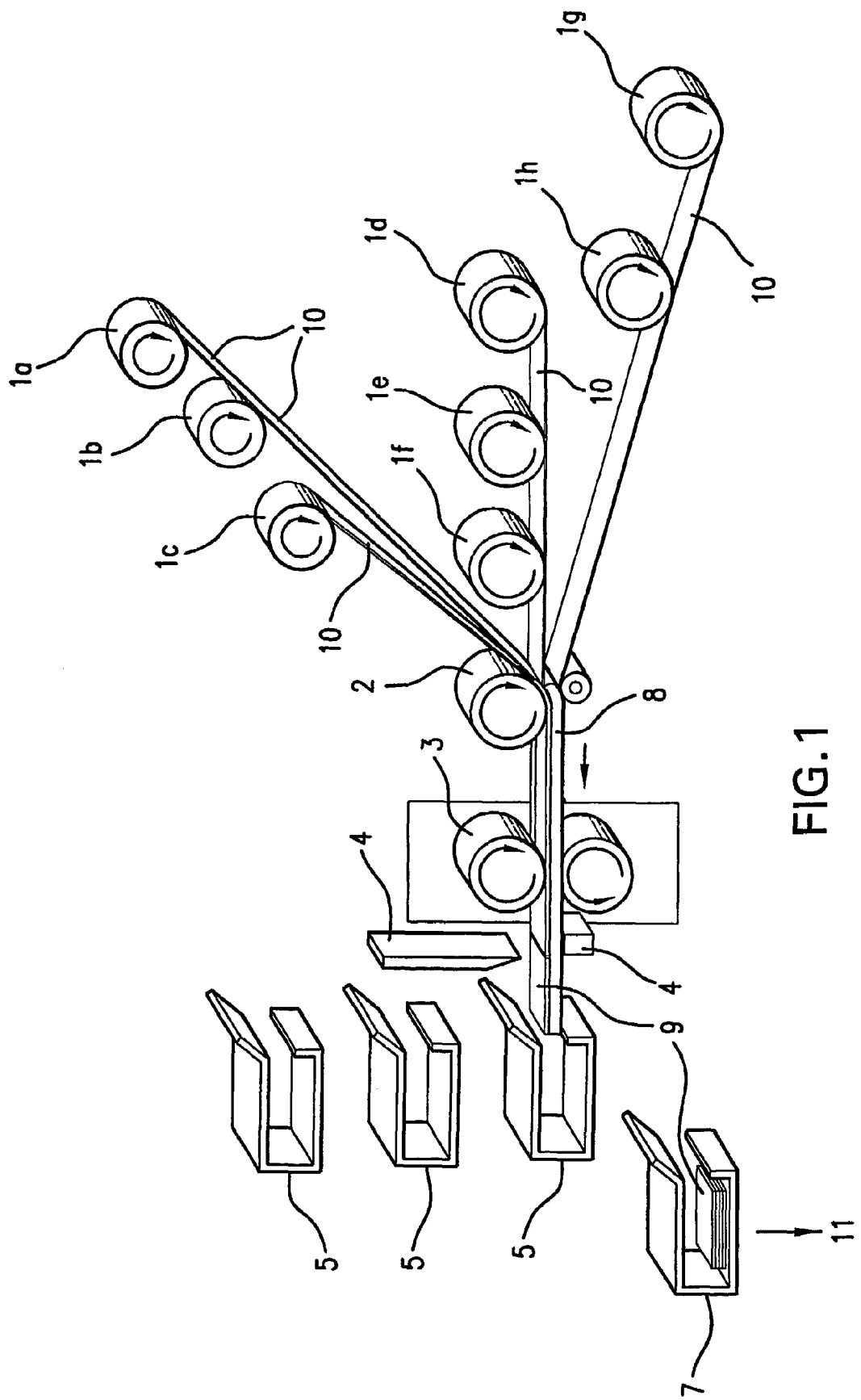
FIG. 1 is a schematic operational view of an embodiment of the invention.

The device for introducing a plurality of individual film-shaped administration forms into a dispenser under formation of a multilayered stack 9 for individually dosable removal comprises according to FIG. 1 an indefinite number (depending on the number of layers) of rolls 1a to 1h with active substance-containing tapes 10 wound thereon.

Said tapes 10, upon being unwound, travel at different angles to the horizontal to guide rolls 2 and pass between said rolls, with the tapes 10 being combined in the process to a multilayered strand 8. Strand 8 is gripped by a pair of conveying rolls 3 and drawn to a cutting device 4. Having reached the end of the transport path, there is severed from the strand 8 by means of the cutting device 4 one multilayered stack 9 at a time, consisting of loose administration forms superimposed upon each other in exact alignment, and filled into a dispensing container 5, which is held ready, after the dispenser 5 having previously been automatically brought to the filling position by means of a conveyor device (not shown). In the process, the dispenser 5 is loaded with at least one stack 9. Depending on the material and on the task to be solved, a dispensing container 5 may also be loaded successively with a plurality of stacks 9. The loaded container is then transported by means of the conveyor device 11.

Figure 2:
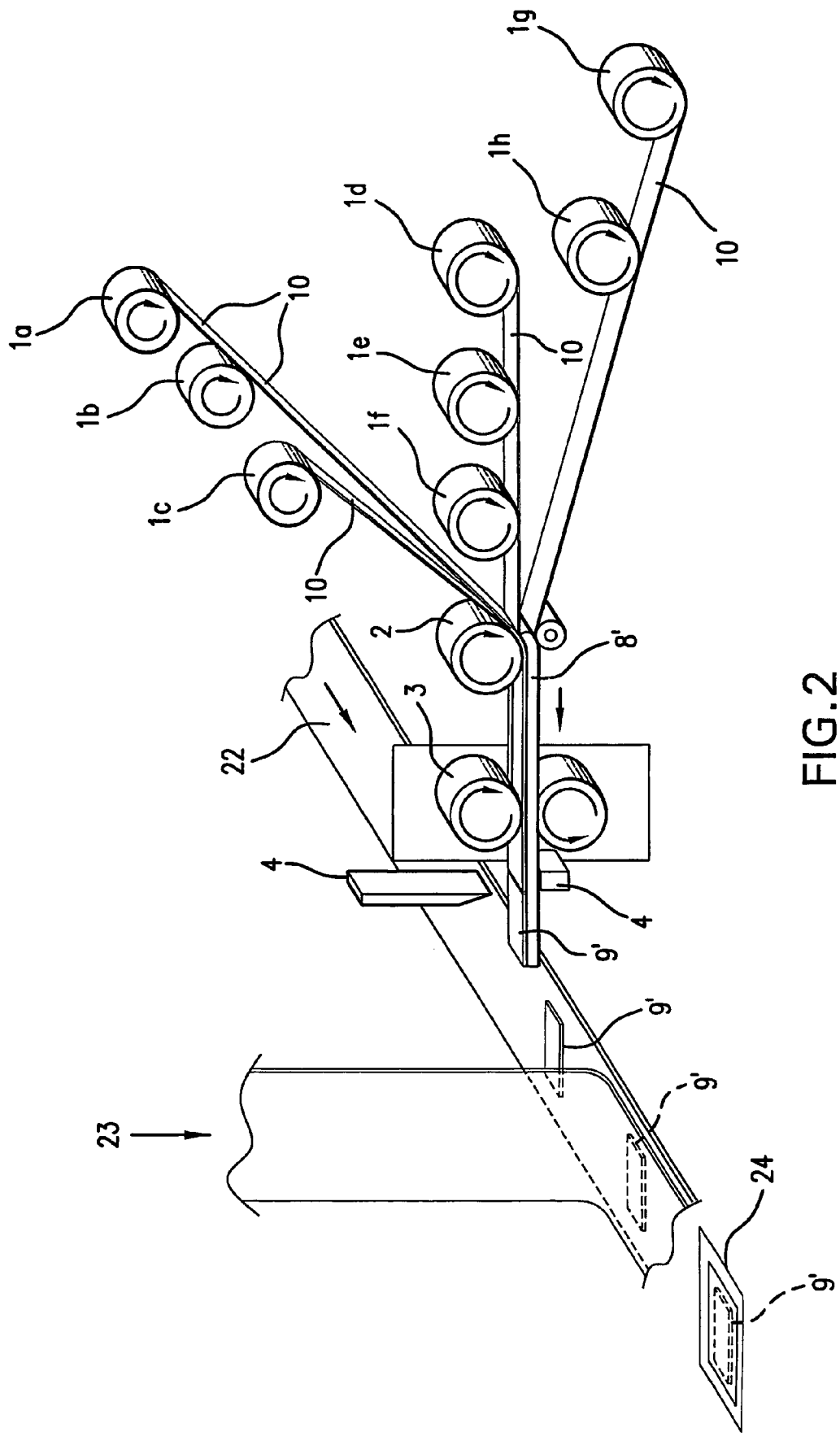
FIG. 2 is a schematic operational view of another embodiment of the invention.

Turning now to FIG. 2, an alternative packaging approach in accordance with the invention is depicted. As mentioned earlier herein, it is possible to fill sealing bags 24 which can be used as a dispenser, for instance, by placing the cut stack 9 on a bottom web 22 of an advancing sealable packaging material, and subsequently, after feeding of an upper web 23 of the packaging material, sealing the resultant bag 24. Thus, the sealable packaging material serves as a dispensing container in place of the particular dispensing container 5 of the embodiment of FIG. 1. Advantageously, the sealable bags 24 can be peelable. A remainder of operation of the embodiment of FIG. 2 is the same as that of FIG. 1.

Figure 3:
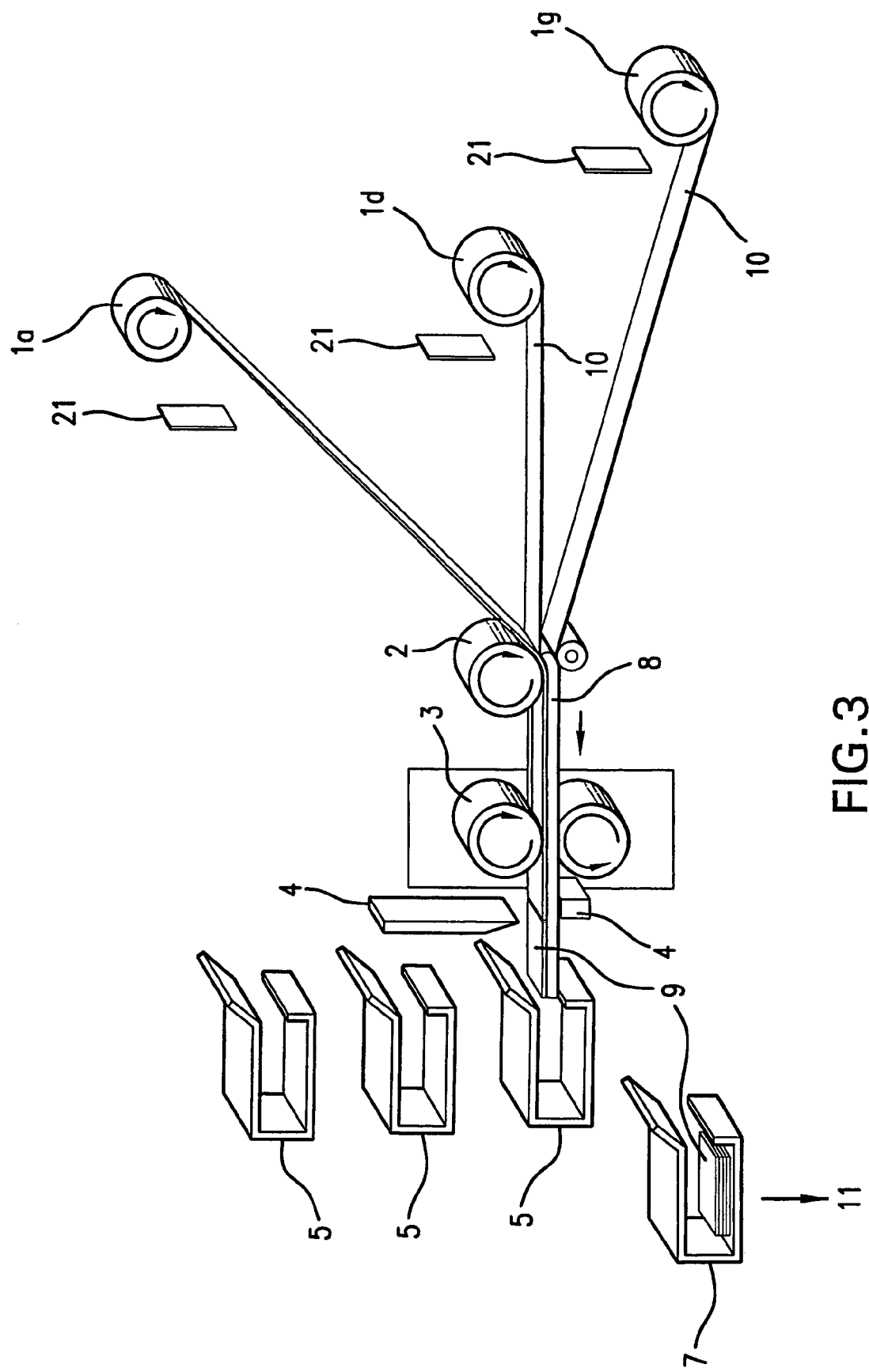
FIG. 3 is a schematic operational view of a further embodiment of the invention.

Drawing of the tapes 10 from their rolls 1 is advantageously supervised optically such that when a tape end appears, the work process is stopped. FIG. 3 shows means for optical supervision 21 which are each located in a position suitable for detecting an appearing end of the tape. It is noted that, for the sake of clarity and to simplify illustration, only three rollers 1a, 1d and 1g are depicted.

Figure 4:
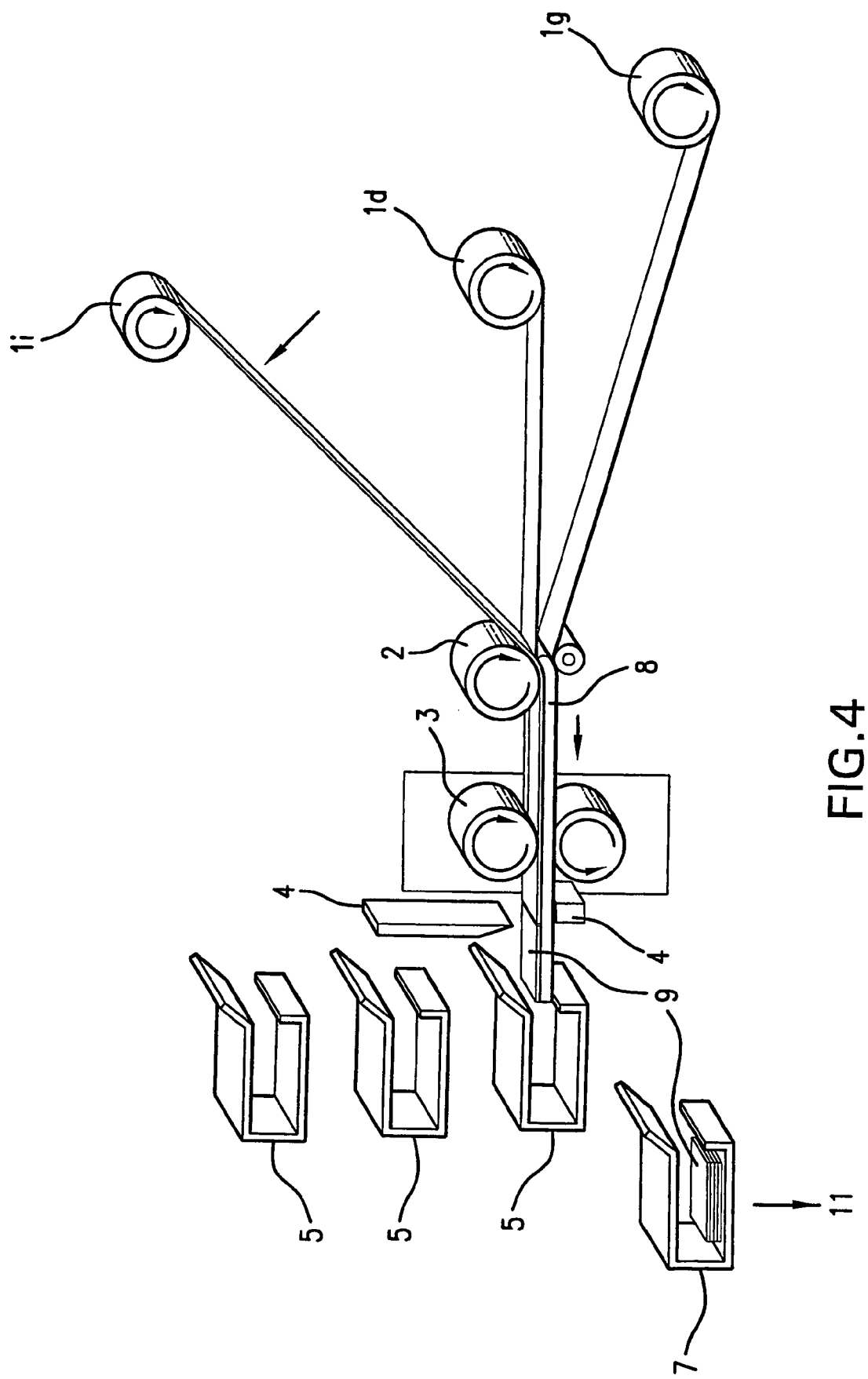
FIG. 4 is a schematic operational view of a still further embodiment of the invention.

According to another aspect of the invention, two or more tapes are wound on a single roll. This is depicted in FIG. 4, wherein roll 1i is shown to have two tapes 20 wound thereon. In such arrangement, top and bottom faces of the two (or more) tapes face in common directions, respectively. It is noted again that only three rollers in total are depicted for simplification purposes.

The process and device in accordance with practice of the invention are surprisingly simple, they can be realized in a cost-effective manner, and offer an ideal solution to the task set at the outset.

The invention claimed is:

1. A method for the production of individual administration forms, arranged as a multilayered stack, from individual tapes, comprising:
   a) arranging said individual tapes into a multilayered strand having a leading end;
   b) aligning and transporting said multilayered strand to a cross-cutting device, such that said leading end of said multilayered strand is advanced beyond said cross-cutting device;
   c) positioning an empty, pre-opened dispenser having an open side in a filling position downstream of said cross-cutting device, such that said open side of said dispenser faces said leading end of said multilayered strand;
   d) shifting said leading end of said multilayered strand substantially into said empty, pre-opened dispenser;
   e) after shifting said leading end substantially into said dispenser, cutting said multilayered strand by means of said cross-cutting device, to sever a multilayered stack from said strand, such that said leading end of said multilayered strand forms a leading end of said multilayered stack; and
   f) transferring said multilayered stack directly into said dispenser.

2. The method according to claim 1, wherein said tapes have a width of between 5 and 40 mm.

3. The method according to claim 1, wherein said administration forms are in the form of a sheet.

4. The method according to claim 1, wherein said administration forms contain at least one of: therapeutic, cosmetic, and food-technological products.

5. The method according to claim 1, wherein said administration forms have a weight per unit area between 10 and 50 g/m$^2$.

6. The method according to claim 1, wherein said dispenser is made of a plastic or cardboard.

7. The method according to claim 1, wherein said dispenser is a sealing bag.

8. The method according to claim 1, wherein said dispenser is a two-piece dispenser with a drawer-shaped bottom part and a top-part.

9. A method for the production of individual administration forms, arranged as a multilayered stack, from individual tapes, comprising:

a) arranging said individual tapes into a multilayered strand having a leading end;

b) shifting said leading end of said multilayered strand substantially into a pre-opened dispenser;

c) after shifting said leading end substantially into said dispenser, cutting said multilayered strand by means of a cross-cutting device, to sever a multilayered stack from said strand; and d) transferring said multilayered stack into said dispenser.

* * * * *